| United States Patent [19] | [11] Patent Number: 4,469,813 |
| Gaaf et al. | [45] Date of Patent: Sep. 4, 1984 |

[54] PROCESS FOR THE PREPARATION OF CATALYTICALLY ACTIVE CROSS-LINKED METAL SILICATES

[75] Inventors: Jan Gaaf, Amsterdam, Netherlands; Rutger A. van Santen, Houston, Tex.

[73] Assignee: Shell Oil Company, Houston, Tex.

[21] Appl. No.: 476,678

[22] Filed: Mar. 18, 1983

[30] Foreign Application Priority Data

Mar. 29, 1982 [NL] Netherlands ................. 8201289

[51] Int. Cl.$^3$ ................. B01J 29/06; C01B 33/26; C01B 33/28
[52] U.S. Cl. ................. 502/263; 502/259; 502/260; 423/327; 423/328; 585/750
[58] Field of Search ............ 252/455 R; 423/327, 423/328

[56] References Cited

U.S. PATENT DOCUMENTS

| 1,926,148 | 9/1933 | Huber ................. 252/450 |
| 3,535,272 | 10/1970 | Kittrell et al. ................. 252/455 R |
| 3,632,500 | 1/1972 | Csicsery et al. ................. 252/455 R X |
| 3,640,904 | 2/1972 | Csicsery et al. ................. 252/455 R |
| 3,729,429 | 4/1973 | Robson ................. 252/455 R X |
| 3,764,519 | 10/1973 | Meyer ................. 252/455 R X |
| 3,803,026 | 4/1974 | Joffe ................. 252/455 R X |
| 3,844,978 | 10/1974 | Hickson ................. 423/328 X |
| 3,844,979 | 10/1974 | Hickson ................. 252/455 R |
| 3,887,454 | 6/1975 | Hickson ................. 252/455 R X |
| 3,909,861 | 10/1975 | Reinhardt et al. ................. 252/442 X |
| 3,944,504 | 3/1976 | Ford et al. ................. 252/455 R |
| 3,966,642 | 6/1976 | Black et al. ................. 252/455 R |
| 4,060,480 | 10/1977 | Reed et al. ................. 208/111 |
| 4,176,090 | 11/1979 | Vaughan et al. ................. 423/327 X |
| 4,216,188 | 8/1980 | Shaftai ................. 423/328 X |
| 4,238,364 | 12/1980 | Shaftai ................. 252/455 R |
| 4,248,739 | 2/1981 | Vaughan et al. ................. 423/328 X |
| 4,271,043 | 6/1981 | Vaughan et al. ................. 252/455 R |
| 4,337,366 | 6/1982 | Fattore et al. ................. 252/455 R X |
| 4,367,163 | 1/1983 | Pinnavoia et al. ................. 252/455 R |

*Primary Examiner*—Delbert E. Gantz
*Assistant Examiner*—William G. Wright
*Attorney, Agent, or Firm*—John M. Duncan

[57] ABSTRACT

Highly active and selective hydroisomerization catalysts are prepared by heating to 300°–450° C. at subatmospheric pressure, a mixture of nickel synthetic mica montmorillonite (Ni-SMM) with a hydroxy aluminum polymeric solution. The resulting pillared Ni-SMM catalyst, preferably Pd-loaded, is especially useful in hydroisomerizing $C_4$–$C_7$ paraffins.

7 Claims, No Drawings

PROCESS FOR THE PREPARATION OF CATALYTICALLY ACTIVE CROSS-LINKED METAL SILICATES

BACKGROUND OF THE INVENTION

The invention relates to a process for the preparation of a catalytically active cross-linked metal silicate. The invention further relates to the use of such metal silicate as a catalyst in the catalytic conversion of hydrocarbons in the presence of hydrogen. The invention also relates to a new catalytically active cross-linked metal silicate.

It is known to use cross-linked metal silicates as catalysts in processes for the conversion of hydrocarbon mixtures, such as cracking and isomerization, with or without the presence of hydrogen.

U.S. Pat. No. 4,176,090 discloses pillared layered clays of the smectite type (e.g., nickel-containing montmorillonite) which have been heated at a temperature of 200°–700° C. However, no vacuum treatment was described.

BRIEF DESCRIPTION OF THE INVENTION

It has now been found that the catalytic activity of cross-linked metal silicates depends on their manner of preparation; in particular it has been found that heating at subatmospheric pressure during preparation has a substantial effect on the performance of the catalyst. For example, the reaction velocity during catalytic hydro-isomerization of straight-chain paraffins is considerably higher when cross-linked metal silicates are used that during their preparation were heated at subatmospheric pressure than when cross-linked metal silicates are used that were not subjected to this treatment at subatmospheric pressure.

The invention therefore relates to a process for the preparation of a catalytically active cross-linked metal silicate wherein a crystalline metal silicate having a crystal lattice largely consisting of a triple layer structure, composed of a center layer of octahedrally coordinated aluminum entirely or partly replaced by nickel and/or cobalt and two outer layers of tetrahedrally co-ordinated silicon partly replaced by aluminum, is mixed with one or more polymerized hydroxy metal complexes, and the mixture is then heated at subatmospheric pressure.

Such stratified metal silicates, which are known by the name of smectites, and which class of compounds includes, inter alia, montmorillonite, are hereinafter referred to as metal silicates.

Particularly suitable metal silicates for the process according to the invention consist at least partly of synthetic mica-montmorillonite in which aluminum has been partly replaced by nickel, which type of substances has been described in Swift, H. E. and Black, E. R. in Ind. Eng. Chem. Prod. Res. Dev. 13 (1974), pp. 106–110, which is incorporated herein by reference. The quantity of nickel in the metal silicates is preferably from 20 to 36% by weight, based on dried non-cross-linked metal silicate.

The metal silicates used in the process according to the invention are preferably prepared via a hydrothermal synthesis route.

A metal silicate consisting of synthetic mica-montmorillonite (SMM) in which aluminum has been partly replaced by nickel synthetic mica montmorillonite (abbreviated: Ni-SMM) can be suitably prepared by entirely or partly replacing the sodium ions in an aqueous dispersion of sodium silicate by protons with the aid of the ion exchanger in the H-form and subsequently adding a nickel salt, an aluminum alcoholate, ammonia and optionally ammonium fluoride. The slurry obtained is partly evaporated and the resultant gel is subsequently heated at 250°–350° C. for several hours in an autoclave. The product obtained after filtration is dried at 70°–200° C.

Ni-SMM can also be suitably prepared by adding a nickel salt, an aluminum alcoholate and ammonium fluoride to an aqueous dispersion of silica, optionally partly evaporating the resultant slurry, adding ammonia, and subsequently introducing the resultant mixture into an autoclave and subjecting it to the same treatment as described in the preparation method first mentioned.

After suspension in water, the nickel-substituted metal silicate prepared by any of the above methods is mixed with one or more polymerized hydroxy metal complexes, preferably largely or entirely consisting of aluminum chlorhydrol (also called aluminum hydroxy chloride). The aluminum chlorhydrol acting as cross-linking agent can suitably be prepared by refluxing aluminum with dilute hydrochloric acid, filtering the resultant solution and subsequently ageing the filtrate for a few days.

The mixture of metal silicate and hydroxy metal complex(es) is preferably heated to a temperature of 300°–450° C., which heating is preferably effected for at least 15 minutes at an absolute pressure of at most 0.1 bar.

Most preference is given to a process according to the invention in which the mixture is heated to a temperature of 340°–420° C. for at least 1 hour, and preferably for at most 100 hours, at an absolute pressure of at most 0.05 bar.

Before the mixture of metal silicate and hydroxy metal complex(es) is heated at subatmospheric pressure, according to the present process the mixture is preferably first subjected to a drying treatment at temperatures from 70° C. to 200° C., followed by calcination at temperatures from 300° C. to 400° C. at atmospheric or elevated pressure.

In the process according to the invention the metal silicate is preferably loaded with one or more noble metals of Group VIII of the Periodic System and/or compounds thereof, as stated on the last page of the "Handbook of Chemistry and Physics", 55th edition, CRC Press, Ohio, U.S.A. (1975).

Before being mixed with hydroxy metal complex(es), the metal silicate is with special preference loaded with 0.2–2% by weight of palladium, based on dried non-cross-linked metal silicate. The loading of the metal silicate with noble metal can be effected by means of any process for the preparation of catalysts known in the art, such as impregnation, ion exchange or precipitation. In the present process it is preferred to apply the Group VIII noble metals to the metal silicate from an aqueous solution containing the metals in the form of cations. Special preference is given to ammonia-containing solutions in which the Group VIII noble metals are present in the form of cationic complexes.

The invention also relates to a process for the catalytic conversion of hydrocarbons, in particular in the presence of hydrogen, with the aid of catalyst prepared according to the process described above.

Before the conversion begins the catalyst is preferably activated by treatment with hydrogen at a temperature from 150° C. to 420° C., in particular for at least several hours at a temperature from 300° C. to 400° C. and at least atmospheric pressure.

It has been found that in the catalytic isomerization of paraffins having 4–7 carbon atoms in the presence of hydrogen, the first order reaction velocity constant is considerably higher (while maintaining a high selectivity (generally above 98%)) when a catalyst is used that has been prepared according to the invention by heating the above-mentioned mixture for some time at subatmospheric pressure than when using a catalyst that has been prepared by heating the same mixture exclusively at atmospheric or elevated pressure.

In the above-mentioned hydroisomerization according to the invention the starting material used is one or more paraffins, especially having 4–7 carbon atoms, preferably consisting substantially or entirely of n-pentane or n-hexane or mixtures of both. Very suitably, an overhead fraction obtained in the atmospheric distillation of petroleum is used as starting material.

It is intended that in the hydroisomerization according to the invention the largest possible proportion of the paraffins present in the feed is converted into isomers of said paraffins with a higher degree of branching, while cracking into products having a smaller number of carbon atoms than the molecules in the feed should be as low as possible.

Suitable conditions for effecting the hydroisomerization according to the invention are:
a temperature between 150° and 330° C.;
a space velocity between 0.2 and 20 kg of paraffin/kg of catalyst/hour;
a hydrogen-paraffin molar ratio from 0.5:1 to 50:1 and a total pressure between 1 and 70 bar.

Very suitable conditions are:
a temperature between 220° C. and 280° C.;
a space velocity between 1 and 5 kg of paraffin/kg of catalyst/hour;
a hydrogen-paraffin molar ratio from 1:1 to 15:1 and a total pressure between 20 and 50 bar.

Another application of the catalysts obtained by the process according to the invention resides in the catalytic hydrocracking of hydrocarbon oils. Catalytically active cross-linked metal silicates are especially suitable for the hydrocracking of relatively large hydrocarbon molecules on account of the ready accessibility of the catalyst for these molecules because of the permanent enlargement of the space between the various triple layers in cross-linked metal silicates in relation to non-cross-linked metal silicates.

In most cases it is not necessary to use pure hydrogen, and hydrogen-containing gases are satisfactory, such as a hydrogen-rich gas obtained in the catalytic reforming of hydrocarbon mixtures.

EXAMPLE I

Preparation of Ni-SSM A

A quantity of 79.7 g of nickel acetate.4 $H_2O$ is dissolved in 200 ml of water, after which in that solution 40 g of dried silica and 47 g of aluminum isopropoxide are consecutively suspended with stirring and 0.82 g of ammonium fluoride is dissolved. Subsequently the resultant mixture is heated at 90° C. for 20 hours with stirring, after which 8 ml of ammonia (25% by weight of $NH_3$) is added and the mixture is heated to 300° C. in the autoclave, which temperature is maintained for 40 hours. Then the autoclave is cooled to ambient temperature and the resultant product is filtered, washed with water and dried at 110° C. The dried product contains 23.2% by weight of nickel.

Preparation of Ni-SSM B

A quantity of 79.2 g of nickel acetate.4 $H_2O$ is dissolved in 335 ml of water, after which to this solution are consecutively added with stirring: 33.3 g of silica, predried for 2 hours at 200° C., 39.2 g of aluminum isopropoxide and 0.68 g of ammonium fluoride. The resultant suspension is evaporated with stirring for 17 hours at a temperature of 90° C. to a volume of 250 ml, after which 6.7 ml of $NH_4OH$ (25% by weight of $NH_3$) is added and the resultant mixture is treated for 40 hours at a temperature of 300° C. in an autoclave. Subsequently, the autoclave is cooled and the product filtered, washed with water and finally dried at 110° C. The resultant clay contains 23.7% by weight of nickel.

Preparation of the cross-linking agent

A quantity of 10.0 g of aluminum strip is refluxed for 5 hours with 50 ml of hydrochloric acid (1N), after which the resultant aluminum chlorhydrol solution, which contains 33 g of aluminum/liter, is filtered off and the filtrate is aged for 10 days before being used as a cross-linking agent. The aluminum chlorhydrol may be described as aluminum chloride in which the chloride ions have been partly replaced by hydroxide ions.

Cross-linking of Ni-SSM A and B

A quantity of 10 g of Ni-SMM (A or B) of the <0.18 mm sieve fraction is suspended in 400 ml of water, after which 50 ml of aluminum chlorhydrol solution, containing 33 g of aluminum/liter, is added and the mixture sitrred for 20 hours at 70° C. Subsequently, the cross-linked Ni-SMM is filtered off, washed with water and dried at 110° C.

The Table below shows the results of X-ray diffraction measurements of 001 lattice spacings for non-cross-linked and for cross-linked Ni-SMM A and B.

TABLE 1

| Sample | 001 lattice spacings in nm | |
|---|---|---|
|  | Non-cross-linked | Cross-linked |
| Ni-SSM A | 1.26 | 1.61 |
| Ni-SMM B | 1.26 | 1.7 |

Table I shows that the 001 lattice spacing is considerably enlarged as a result of the cross-linking of the Ni-SSM.

Preparation of catalyst A

A quantity of 5 g of the dried, non-cross-linked Ni-SSM A is suspended in a solution of 83 mg of $Pd(NH_3)_4Cl_2.H_2O$ in 100 ml of water and stirred for 16 hours, after which the product is washed with 200 ml of water, filtered off and dried at 110° C. The resultant product contains 0.7% by weight of palladium and is subsequently cross-linked in the same way as described above under "Cross-linking of Ni-SMM A and B".

After drying, the cross-linked and palladium-loaded Ni-SSM A is calcined for 2 hours at 350° C. in air at atmospheric pressure and subsequently heated at 350° C. for 16 hours at an absolute pressure of $1 \times 10^{-6}$ bar.

The resultant catalyst A is pressed into tablets and ground in a mortar, after which the catalyst particles of the 0.18–0.59 mm sieve fraction are heated at 350° C.

and an absolute pressure of $1\times10^{-6}$ bar for a further 4 hours.

Preparation of catalyst B

A quantity of 5 g of the dried cross-linked Ni-SMM B is suspended in a solution of 83 mg of $Pd(NH_3)_4Cl_2.H_2O$ in 100 ml of water and stirred for 16 hours, after which the product is washed with 200 ml of water, filtered off and dried at 110° C. The resultant product contains 0.7% by weight of palladium and is subsequently calcined in air at 400° C. for 2 hours at atmospheric pressure and subsequently heated for 16 hours at 400° C. and an absolute pressure of $1\times10^{-6}$ bar.

The resultant catalyst B is pressed into tablets, ground in a mortar and the catalyst particles of the 0.18–0.59 mm sieve fraction are heated at 400° C. and an absolute pressure of $1\times10^{-6}$ bar for a further 4 hours.

Preparation of catalyst C

After drying, the cross-linked and palladium-loaded Ni-SMM A, as obtained in the preparation of catalyst A, is calcined in air for 2 hours at 350° C. and at atmospheric pressure.

Preparation of catalyst D

After drying, the cross-linked and palladium-loaded Ni-SMM B obtained in the preparation of catalyst B is calcined at 400° C. and at atmospheric pressure for 2 hours.

The catalysts A and B have been prepared in accordance with the process of the invention; C and D are comparative catalysts not according to the invention.

EXAMPLE II

Hydroisomerization of pentane

Pentane hydroisomerization experiments are carried out in a microflow reactor with a length of 35 cm and an internal diameter of 1 cm, containing 2 g of catalyst particles (of the 0.18–0.59 mm sieve fraction).

Before being used for the catalytic conversion of hydrocarbons, the catalysts A, B, C and D are treated with hydrogen in the isomerization reactor at a pressure of 1 bar and a temperature of 343° C. for 16 hours.

After the activation treatment of the catalyst with hydrogen has taken place at 343° C. in the microflow reactor, the temperature of the latter, both for the use of catalyst A and of B, C and D, is reduced to 250° C. and the pre-dried n-pentane feed is subsequently passed across the catalyst together with pure hydrogen.

The reaction conditions of the hydroisomerization step are:
temperature : 250° C.
total pressure : 30 bar
hydrogen/pentane molar ratio: 1.25
space velocity : 2 g of pentane/g of catalyst/hour.

The product stream is continuously analyzed by means of gas-liquid chromatography.

In Table II below, "k" is the first order reaction velocity constant expressed in g of converted pentane per g of catalyst per hour, and "Selectivity, %" is the percentage by weight of isomerized pentane based on converted pentane.

The results of experiments according to the invention are stated against Nos. 1 and 2. Nos. 3 and 4 are comparative experiments, not according to the invention.

TABLE II

| Exp. No. | Catalyst | Temp. (°C.) of calcination (press. = 1 bar) | Temp. (°C.) of the vacuum treatment | k (gram. $gram^{-1}.h^{-1}$) | Selectivity, % |
|---|---|---|---|---|---|
| 1 | A | 350 | 350 | 3.6 | 98.8 |
| 2 | B | 400 | 400 | 2.3 | 98.1 |
| 3 | C | 350 | — | 0.5 | 99.6 |
| 4 | D | 400 | — | 2.0 | 97.3 |

The heating of cross-linked Ni-SMM at subatmospheric pressure results in a higher k-value for the hydroisomerization of pentane while maintaining high selectivity, in comparison with the use of cross-linked Ni-SMM which has been calcined at exclusively atmospheric pressure.

What is claimed is:

1. A process for the preparation of catalytically active cross-linked metal silicates wherein a crystalline metal silicate having a crystal lattice largely consisting of a triple layer structure, composed of a center layer of octahedrally co-ordinated aluminum entirely or partly replaced by nickel and/or cobalt and two outer layers of tetrahedrally co-ordinated silicon partly replaced by aluminum, is mixed with one or more polymerized hydroxy metal complexes, and the mixture is then dried at temperatures of from 70° C.–200° C., subsequently calcined at temperatures of 300° C.–400° C. at atmospheric or elevated pressure, and is subsequently heated to a temperature of 300°–450° C. for at least 15 minutes at an absolute pressure of at most 0.1 bar.

2. The process of claim 1 wherein the metal silicate consists at least partly of synthetic mica-montmorillonite in which aluminum has been partly replaced by nickel.

3. The process of claim 2 wherein the polymerized hydroxy metal complex used is aluminum chlorhydrol.

4. The process of claim 1 wherein the mixture is heated to a temperature of 340° C.–420° C. for at least one hour.

5. The process of claim 1 wherein the mixture is heated for at least one hour at a temperature of 340° C.–420° C. and at an absolute pressure of at most 0.05 bar.

6. The process of claim 1 wherein the metal silicate is loaded with one or more noble metals of Group VIII of the Periodic System and/or compounds thereof.

7. The process of claim 6 wherein before mixing with hydroxy metal complex(es) the metal silicate is loaded with 0.2–2% by weight of palladium, based on dried non-cross-linked metal silicate.

* * * * *